United States Patent [19]

Sommermeyer et al.

[11] Patent Number: 5,218,108

[45] Date of Patent: Jun. 8, 1993

[54] HYDROXYLETHYLSTARCH (HES) AS PLASMA EXPANDER AND PROCESS FOR PREPARING HES

[75] Inventors: Klaus Sommermeyer; Franz Cech; Burghard Weidler, all of Rosbach; Klaus Henning, Usingen, all of Fed. Rep. of Germany

[73] Assignee: Fresenius AG, Bad Homburgh, Fed. Rep. of Germany

[21] Appl. No.: 533,294

[22] Filed: Jun. 5, 1990

[30] Foreign Application Priority Data

Jun. 16, 1989 [DE] Fed. Rep. of Germany ....... 3919729

[51] Int. Cl.$^5$ .................... C08B 31/10; A61K 31/72
[52] U.S. Cl. ...................................... 536/111; 514/60
[58] Field of Search .......................... 536/111; 514/60

[56] References Cited

U.S. PATENT DOCUMENTS

| | | | |
|---|---|---|---|
| 4,474,951 | 10/1984 | Pope | 536/111 |
| 4,629,698 | 12/1986 | Nitsch et al. | 435/98 |
| 4,716,186 | 12/1987 | Portnoy et al. | 536/111 |
| 4,837,314 | 6/1989 | Eastman | 536/111 |

FOREIGN PATENT DOCUMENTS 935339 8/1963 United Kingdom .

*Primary Examiner*—Nathan M. Nutter
*Attorney, Agent, or Firm*—Omri M. Behr; Matthew J. McDonald

[57] ABSTRACT

A hydroxyethyl starch for use as plasma expander which is obtainable by hydrolytic predegradation of a starch rich in amylopectin, partial hydroxyethylation to a specific substitution degree in the presence of alkali and subsequent hydrolytic degradation to a specific molecular weight, comprises a mean molecular weight of 60,000–600,000 and a substitution degree MS of 0.15–0.5. The ratio of the substitution of C2 to the substitution of C6 of the anhydroglucose units is 8–20 and the substitution degree DS lies in the range from 0.15 to 0.5. A process for the preparation of this hydroxyethyl starch employs 2-chloroethanol as hydroxyethylation agent. The hydroxyethylation is carried out under alkaline conditions at room temperature, the pH value held at a value of about 12 and the temperature held at a value of about 20° C.

7 Claims, No Drawings

HYDROXYLETHYLSTARCH (HES) AS PLASMA EXPANDER AND PROCESS FOR PREPARING HES

The field of volume substitution (e.g. hemorrhagic shock) or hemodilution (e.g. arterial occlusive disease, Fontaine II B, III) is today inconceivable without the use of colloidal plasma substitutes. For both these indications, of the exogeneous plasma substitutes (starch, gelatins, dextran), hydroxyethyl starch (HES) has found the greatest acceptance in recent years.

The lower disturbance of coagulation and the clearly reduced incidence of serious anaphylactoid reactions compared with dextran are responsible for the good acceptance of hydroxyethyl starch in the field of volume replacement and hemodilution. In addition, it has been possible to show that the volume efficacy of hydroxyethyl starch, depending on the indication, may be referred to as sufficient to good, a differentiated therapy being possible, depending on the state of the patient, by using the various known hydroxyethyl starch preparations differing in molecular weight and substitution degree. The factor considered particularly favourable here is the low colloid osmotic pressure of starch solutions compared with dextrans. With regard to the kidneys, the lower urine viscosity involves a lesser risk of a decrease in functional activity. In the area of hemodilution, in addition to the reduction of hematocrit, the reduction of plasma viscosity in particular has proved to be a therapeutically effective principle of HES-induced rheological improvement. Therapeutical advantages are obtained over other exogeneous plasma substitutes.

Already known hydroxyethyl starches used as plasma expanders have different molecular weights $M_w$ and substitution degrees MS and DS as well as different substitution patterns.

Due to the use of the natural starting raw material amylopectin and the production process in which to a certain extent a cleaving of the polymer chains is necessary, the hydroxyethyl starch is not present as molecular unitary substance with defined molecular weight but as mixture of molecules of different size which are also differently substituted by hydroxyethyl groups. The characterization of such mixtures requires the aid of statistically determined magnitudes (cf. K. Sommermeyer et al., "Clinically employed hydroxyethyl starch: physical chemical characterization", Krankenhauspharmazie, 271 (1987)). To denote the average molecular weight, the mean molecular weight $M_w$ is used. The general definition of this mean value is:

$$M_w = \frac{\sum_i N_i \cdot M_i^w}{\sum_i N_i \cdot M^{w-1}}$$

There are two differently defined substitution degrees for defining the substitution by hydroxyethyl groups.

The substitution degree MS (molar substitution) is defined as the average number of hydroxyethyl groups per anhydroglucose unit. It is determined from the total number of hydroxyethyl groups in a specimen, for example in accordance with Morgan, by ether splitting and subsequent quantitative determination of ethyl iodide and ethylene, which are thereby formed.

In contrast, the substitution degree DS (degree of substitution) is defined as the proportion of the substituted anhydroglucose units of all anhydroglucose units. It can be determined from the measured amount of the unsubstituted glucose after hydrolysis of a specimen. It follows from these definitions that MS>DS. In the case where only monosubstitution is present, i.e. each substituted anhydroglucose unit carries only one hydroxyethyl group, MS=DS.

It is known that α-amylase breaks down hydroxyethyl starches in the sense that only glycosidic bonds of unsubstituted anhydroglucose units are split. It is further known that with increasing degree of substitution MS or DS the elimination of hydroxyethyl starches from the plasma is retarded.

It is moreover known that for the same MS, DS and the same molecular weight distribution starches substituted mainly in the 6-position are eliminated faster than starches substituted mainly in the 2-position.

In this respect, only hydroxyethyl starches having a low C2/C6 ratio or being highly substituted were used for pharmaceutical purposes.

Thus, GB-PS 1,395,777 describes hydroxyethyl starches substituted predominantly in 6-position corresponding to a C2/C6 ratio of 0.5 to 2.0. These hydroxyethyl starches are made by reaction of wax maize starch with ethylene oxide with alkali in excess.

DE-OS 2,814,032 describes a process for preparing hydroxyl starch suitable as blood plasma expander, the starch being alkaline hydroxyethylated, the reaction mixture then neutralized and the hydroxyethyl starch formed extracted from the reaction mixture with a solvent, such as dimethyl formamide in which the salts formed by the neutralization are only sparingly soluble or not soluble at all. The hydroxyethyl starch obtained has a molar ratio of 2-O-hydroxyethyl anhydroglucose to 6-O-hydroxyethyl anhydroglucose of about 1.

According to the process described in DE-OS 3,313,600 for preparing plasma expanders on a starch basis in which the degradation step of the starch rich in amylopectin is at least partially carried out enzymatically, the breaking down of the starch is performed to a molecular weight of 40,000 to 1,000,000 Dalton, in particular from 200,000 to 450,000 Dalton, and the etherification to a substitution degree (MS) of 0.1 to 0.8 or 0.5 to 0.8, in particular 0.5 to 0.7 (cf. page 8, paragraph 3). The ratio of the substitution of C2 compared with the substitution of C6 is low (cf. page 5, paragraph 2).

The aforementioned hydroxyethyl starches have the disadvantage that they do not ensure a complete degradability from the plasma within a period of about 6–12 hours and moreover, due to their high substitution degree MS (MS>0.5), involve the danger that with the usual repetition infusions over longer periods of time an accumulation of difficultly eliminatable components takes place in the serum and tissue. Due to this long-time storing, allergic reactions may occur, for example nettle rash, etc.

The problem underlying the invention is therefore to make available a hydroxyethyl starch which can be completely broken down within a physiologically reasonable time.

A further problem resides in making available an HES which nevertheless due to the choice of a suitable MS or DS value and the molecular weight has a controllable elimination behaviour.

The starting products for recovering hydroxyethyl starch are starches having a high content of amylopectin, the highly branched component of starch, in particular potato starch, wax maize starch, sorghum starch or waxy rice starch.

For a coarse presetting of the intended molecular weight these starches are subjected to a hydrolytic degradation reaction. The molecular weight is reduced here from about 20,000,000 Dalton to several million Dalton.

In the subsequent alkaline hydroxyethylation with known hydroxyethylation agents, it is possible to introduce a hydroxyethyl group into position 2, 3 and 6 of the anhydroglucose unit. Disubstituted units, such as 2,3-dihydroxyethyl anhydroglucose, 2,6-dihydroxyethyl anhydroglucose are formed in the synthesis with less probability. The reactivity of the individual hydroxy groups in the unsubstituted anhydroglucose unit compared with hydroxyethylation is different depending on the reaction conditions. Within certain limits, the substitution pattern, i.e. the individual differently substituted anhydroglucoses statistically shared amongst the individual polymer molecules, can thereby be influenced. Advantageously, predominantly the 2 and the 6-position is hydroxyethylated, the 6-position being preferred due to easier accessibility.

The objective of the present invention, that is the preparation of a hydroxyethyl starch which can be completely broken down within a physiologically reasonable period and which on the other hand nevertheless has a controllable elimination behaviour, is achieved by a starch substituted predominantly in 2-position and substituted as homogeneously as possible, MS being approximately equal to DS.

The predominant 2-substitution makes the hydroxyethyl starch relatively difficult to degrade for $\alpha$-amylase. It is advantageous to avoid as far as possible the occurrence of substituted anhydroglucose units one behind the other within the polymer molecule in order to guarantee complete degradability.

This can be achieved in that the substitution is accordingly low, enabling the molecules to derivate statistically in the sense of a substitution distributed over the total molecules. This results in substituted anhydroglucoses at a relatively large distance apart, compensating the effect of the retardation of the $\alpha$-amylase degradation due to the predominant 2-substitution and enabling a controllability of the degradation rate to be achieved.

It has been found that hydroxyethyl starches substituted extremely low (MS<0.5) and having a high ratio of the substitution of C2 to the substitution of C6 of the anhydroglucose units are rapidly and completely eliminated from the human body within the first hours of the infusion.

It has further been found that such hydroxyethyl starches, in spite of the low substitution, contrary to the opinion of those skilled in the art, do have an adequately high solubility in aqueous medium so that the solutions are stable even for relatively long periods of time and do not form any agglomerates or gels which would make the further use as plasma expander solution impossible.

Hydroxyethyl starches with the characteristics described above therefore combine the general advantages of hydroxyethyl starch compared with other plasma expander types, such as gelatins or dextran, and avoids the disadvantages of the hitherto known hydroxyethyl starch types used for the indications described.

Hydroxyethyl starches having the aforementioned properties can be obtained with the aid of a process including essentially the following steps:

a) Preextraction of the starch used with methanol to remove vegetable dyes and to block reactive groups. Thus, for example, reactive aldehyde groups are partially inactivated by acetal formation.

b) Methanolic hydrolysis for coarse setting of the molecular weight with a 20-40%, preferably 30% methanolic suspension of the starch with 1% HCl, the latter being held for 2-4 h, preferably 3 h, at 30°-50° C., preferably 40° C. The end of the reaction is achieved by neutralization with 1 NaOH and subsequent cooling to room temperature. Thereafter the suspension is washed free of chloride.

c) Alkali wash for protein extraction, a 30-50%, preferably 40% suspension in 0.1 N NaOH being prepared and this being held 1-3 h, preferably 2 h, at 30°-50° C., preferably 40° C. Thereafter the procedure is repeated at room temperature.

d) Hydroxyethylation with a hydroxyethylating agent, for example ethylene oxide, and in a particularly preferred embodiment, 2-chloroethanol, the molar ratio of pretruded starch to hydroxyethylating agent being adapted to the desired substitution degree. The starch is dissolved under nitrogen in 20-40%, preferably 30% suspension, in 1 N NaOH for 2 h at 30°-50° C., preferably 40° C. Within 6-10 hrs., preferably 7-8 hrs., the hydroxyethylating agent is added in drops at room temperature, the addition of 10 N NaOH preventing the pH value dropping below 12. Thereafter, this is neutralized with 10% HCl.

e) The solution is heated to 40°-70° C., preferably 60° C., mixed with 0.2% HCl and the hydrolysis followed viscosimetrically. The reaction is terminated by neutralization with NaOH and cooling to room temperature.

f) Purification by filtration through a depth filter and ultrafiltration through a hollow fibre module with a separating limit of about 30,000 Dalton.

g) Spray drying of the end products in a manner known per se.

The hydroxyethyl starches according to the invention are also suitable as carbohydrate components in enteral nutrition of diabetics because the same considerations apply as regards the degradability.

The invention will be explained in detail hereinafter with the aid of an example.

500 g wax maize starch is suspended in a litre of dry methanol and brought to boil. After cooling the methanol is sucked off and the starch washed with water. The washing operation is repeated once.

The starch with a residual moisture content of 28.13% is hydrolyzed in 30% methanolic suspension with 1% HCl for three hours at 40° C. The reaction is stopped by neutralization with 1 N NaOH in methanol and cooling to room temperature. After extraction the starch exhibits a residual moisture content of 16.12% and a mean molecular weight of 900,000.

The starch is suspended in a litre H2O, extracted and washed free of chloride. After suction drying the starch has a residual moisture content of 51.29%.

The starch is thereafter stirred in 40% suspension in 0.1 N NaOH for 2 hours at 40° C., again cooled to room temperature and dried by exhaustion (residual moisture content 48.60%). The operation is repeated once at room temperature.

418.0 g (2.58 Mol) of pretreated starch are dissolved in 30% suspension in 1 N NaOH at 40° C. under nitrogen. Within 7–8 hrs., 51.9 ml (0.77 Mol) 2-chloroethanol is dripped in. By adding NaOH reduction of the pH value below 12 is avoided. Thereafter, neutralization is carried out with 10% HCl.

The solution is filtered after 1:1 dilution with water via a depth filter (Seitz T750).

The solution is thereafter heated to 60° C., set with 25% HCl to an HCl concentration of 0.2 and hydrolyzed for 4 hours.

The solution is neutralized by addition of sodium hydroxide to pH 6.0 and cooled to room temperature. Thereafter, filtration is carried out via a Seitz EKS filter.

The clear solution is now ultrafiltrated via a hollow fibre module with a separation limit of about 30,000 Dalton and the remaining retentate spray dried.

A hydroxyethyl starch is obtained having a mean molecular weight of 234,000 and a molar substitution degree of 0.26. The C2/C6 ratio is 9.34. The hydroxyethyl starch prepared in this manner has the following substitution pattern (area percentages) which can be determined by complete hydrolysis of HES and subsequent determination of glucose and its hydroxyethyl derivatives via trimethyl silylation:

| glucose: | 81.42% |
|---|---|
| 2-O-hydroxyethyl glucose: | 12.42% |
| 3-O-hydroxyethyl glucose: | 2.70% |
| 6-O-hydroxyethyl glucose: | 1.33% |
| 2,2-O-dihydroxyethyl glucose: | 0.21% |
| 2,3-O-dihydroxyethyl glucose: | 0.51% |
| 2,6-O-dihydroxyethyl glucose: | 0.17% |
| 3,3-O-dihydroxyethyl glucose: | 0.10% |
| 3,6-O-dihydroxyethyl glucose: | 0.05% |

We claim:

1. Hydroxyethyl starch for use as plasma expander obtainable by hydrolytic pre-degradation of a starch rich in amylopectin, partial hydroxyethylation up to a certain substitution degree in the presence of alkali and subsequent hydrolytic degradation to a certain molecular weight, characterized in that it has a mean molecular weight of 60,000–600,000 and a substitution degree MS of 0.15 to 0.5,
the ratio of the substitution of C2 to the substitution of C6 of the anhydroglucose units is 8–20 and the substitution degree DS lies in the range from 0.15 to 0.5.

2. Hydroxyethyl starch according to claim 1, characterized in that it has a mean molecular weight of 80,000 to 400,000 and a substitution degree MS of 0.2–0.4, the ratio of the substitution of C2 to the substition of C6 of the anhydroglucose units is 8–20 and the substitution degree DS lies in the range from 0.15 to 0.40.

3. Hydroxyethyl starch according to claim 1, characterized in that it has a mean molecular weight of 100,000 to 300,000 and a substitution degree MS of 0.25–0.35, the ratio of the substitution of C2 to the substitution of C6 of the anhydroglucose units is 8–20 and the substitution degree DS lies in the range from 0.2 to 0.35.

4. A hydroxyethyl starch for use as plasma expander characterized in that it has a mean molecular weight of 60,000–600,000 and a substitution degree MS of 0.15 to 0.5,
the ratio of the substitution of C2 to the substitution of C6 of the anhydroglucose units is 8–20 and
the substitution degree DS lies in the range from 0.15 to 0.5, produced by a process wherein:
a) starch having a content of amylopectin of >95% is pre-extracted with methanol,
b) the starch is brought by acid hydrolysis to a suitable mean molecular weight,
c) the starch is subjected to an alkali wash,
d) the starch is hydroxyethylated by means of a hydroxyethylation agent under alkaline conditions,
e) the molecular weight is exactly set by acid hydrolysis,
f) the hydroxyethyl starch thus obtained is pulled, and
g) spray dried,
characterized in that the hydroxyethylation agent used is selected from the group consisting of 2-chloroethanol and ethylene oxide and the hydroxyethylation is carried out under alkaline conditions at room temperature.

5. A starch of claim 4 characterized in that the pH value is kept at a value of about 12 during the hydroxyethylation.

6. A starch of claim 4 characterized in that the temperature is kept at a value of about 20° to 25° C.

7. A starch of claim 4 characterized in that the hydroxyethyl starch is purified by filtration and ultrafiltration.

* * * * *